United States Patent [19]

Uchiyama et al.

[11] 4,407,745
[45] Oct. 4, 1983

[54] HEPTACOSAPEPTIDE

[75] Inventors: Mikio Uchiyama, Urawa; Takashi Sato, Tokyo; Hiroshi Yoshino, Abiko; Yutaka Tsuchiya, Tokyo; Masayuki Konishi, Ichinomiya; Masahiko Tsujii, Kagamihara; Yoshihiko Hisatake, Kounan; Atsushi Koiwa, Gifu, all of Japan

[73] Assignee: Eisai Co., Ltd., Tokyo, Japan

[21] Appl. No.: 300,857

[22] Filed: Sep. 10, 1981

[30] Foreign Application Priority Data

Sep. 11, 1980 [JP] Japan .................... 55-125262

[51] Int. Cl.³ .......................... C07C 103/52
[52] U.S. Cl. ............................. 260/112.5 R
[58] Field of Search ............... 424/177; 260/112.5 R

[56] References Cited

U.S. PATENT DOCUMENTS

| | | | |
|---|---|---|---|
| 3,400,118 | 9/1968 | Bodanszky et al. | 260/112.5 R |
| 3,417,072 | 12/1968 | Bodanszky et al. | 260/112.5 R |
| 3,767,639 | 10/1973 | Bodanszky et al. | 260/112.5 R |
| 3,812,091 | 5/1974 | Ondetti | 260/112.5 R |
| 3,812,092 | 5/1974 | Bodanszky et al. | 260/112.5 R |
| 4,086,220 | 4/1978 | Schlatter | 260/112.5 R |
| 4,167,508 | 9/1979 | Wünsch | 424/177 |

OTHER PUBLICATIONS

Chem. Ber. 107, 215-231 (1974).
Rec. Tran. Chim. Pays. Bas. 93, 256,257 (1974).
Naturwissenchaften 59, 239-246 (1972).
Bull. Chem. Soc. of Japan 51,(11) 3409-3410, (1978).
Helv. Chim. Acta 59 (1976), 1112-1126.
J. of Med. Chem. (1977), 20, (5) 648-655.

Primary Examiner—Delbert R. Phillips
Attorney, Agent, or Firm—Flynn, Thiel, Boutell & Tanis

[57] ABSTRACT

A heptacosapeptide having the following structural formula:

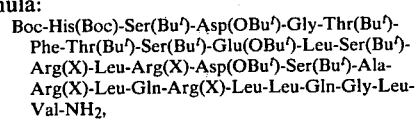

in which X is a group having the formula:

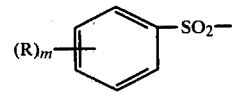

where R is an alkyl or alkoxy and m is an integer of 1 to 3, provided that R's may be the same or different in case m is 2 or 3. The heptacosapeptide may be converted to a secretin.

11 Claims, No Drawings

HEPTACOSAPEPTIDE

The present invention relates to a novel heptacosapeptide and preparation of secretin from it. More particularly, the present invention relates to a novel peptide valuable as an intermediate for use in synthesizing secretin advantageously on an industrial scale.

Secretin which is one of the digestive canal hormones is a peptide consisting of 27 amino acids as is seen from the following formula and since it has medically valuable actions of promoting the pancreatic external secretin, controlling gastrin-stimulated secretin of the stomach acid, releasing insulin, stimulating secretin of pepsin and decomposing fat, it is used as a pancreatic function-examining agent, a medicine for curing duodenal ulcers and the like:

H.His—Ser—Asp—Gly—Thr—Phe—Thr—Ser—Glu—Leu—Ser—Arg—    [I]
  1   2   3   4   5   6   7   8   9   10  11  12

Leu—Arg—Asp—Ser—Ala—Arg—Leu—Gln—Arg—Leu—Leu—Gln—Gly—Leu—Val—NH$_2$
 13  14  15  16  17  18  19  20  21  22  23  24  25  26  27

Secretin has heretofore been obtained from the duodenum of a pig by extraction [see, for example, H. Penau et al.; Soc. Chimie Bicel., 7, 17 (1925)]. This extraction process is defective in that the process steps are complicated and the starting material is not readily available. Furthermore, inclusion of impurities that can hardly be separated, such as cholecystokinin and pancreozymin, cannot be avoided.

Accordingly, many proposals have heretofore been made to prepare secretin according to synthesis processes.

Such synthesis processes have been proposed by M. Bodanszky et al. [J. Am. Chem. Soc., 90, 4711 (1968)], E. Wünsch et al. [Naturwissenschaften, 59, 239 (1972)], G. Jäger et al. [Chem. Ber., 107, 215 (1974)], H. C. Beyerman et al. [Helv. Chim. Acta., 59, 1112 (1976)], B. Hemmasi [Int. J. Peptide Protein Rec., 9, 63 (1977)], and Yanaihara et al. [J. Med. Chem., 20, 654 (1977)]. However, in these known processes, it is hardly examined how to prepare secretin in a large amount at a high efficiency, and therefore, any of these processes cannot be regarded as a process for synthesizing secretin industrially advantageously. Since secretin is a peptide comprising 27 amino acids as structural ingredients as described above, when it is intended to obtain secretin at a high purity in a high yield on an industrial scale, there should be solved various difficult problems in connection with, for example, the kind of the protective group to be selected and conditions for removing the protective group.

In the foregoing known processes, various impurities which can hardly be separated are formed because of difficulties in preparing starting protected amino acids and incomplete protection of side chain functional groups by protective groups, and therefore, purification is very difficult. Furthermore, the yield at the step of forming final secretin from an expensive protected secretin containing protective groups, which is synthesized through scores of steps, is very low and the purity of the obtained final product is not satisfactorily high. Therefore, these known processes are not suitable as industrial processes.

Japanese Patent Application Laid-Open No. 12516/77 proposes a process for solving the foregoing problems.

According to this process, the condensation catalyst is improved to shorten the condensation time, a peptide having the following structural formula [II]:

Boc-His-Ser(Bu$^t$)-Asp(OBu$^t$)-Gly-Thr(Bu$^t$)-Phe-
Thr(Bu$^t$)-Ser(Bu$^t$)-Glu(OBu$^t$)-Leu-Ser(Bu$^t$)-Arg-
Leu-Arg-Asp(OBu$^t$)-Ser(Bu$^t$)-Ala-Arg-Leu-Gln-
Arg-Leu-Leu-Gln-Gly-Leu-Val-NH$_2$    [II]

is synthesized as a protected secretin, protective groups are removed, and purified secretin is obtained in a yield of 22% from the resulting crude secretin by using an alkylated dextran gel (LH-20) and also using 0.005 N cysteine hydrochloride or 0.001 N hydrochloric acid aqueous solution for elution.

The yield and purity of secretin obtained as the final product in this process are not satisfactorily high. More specifically, when 0.005 N cysteine hydrochloride is used, the secretin activity is 2600 cu/mg and the peptide content is 65%, and the product contains 5% of cysteine hydrochloride, and when 0.001 N hydrochloric acid aqueous solution is used, the secretin activity is 2600 to 2700 cu/mg and the peptide content is 70%. The activity as the dry feed base, that is, the activity based on the peptide, is 4000 cu/mg in the former case and is 3714 to 3857 cu/mg in the latter case. These activity values are lower than the activity value of pure natural secretin, namely 4000 cu/mg in case of the acetate or 5000 cu/mg in case of the dry free base [see Gut. 19, 355 (1978)].

We made researches with a view to developing industrial processes for the synthesis and purification of secretin having a higher activity, and we succeeded in developing a process for obtaining high-activity and high-purity synthetic secretin having a secretin activity of about 4500–4600 cu/mg and a peptide content of about 86–87% as determined by the amino acid analysis, that is, a dry free base activity of about 5200–5300 cu/mg, in a yield of about 66–73% from a protected secretin.

The protected secretin that is used in the present invention is a novel heptacosapeptide having the following structural formula:

Boc-His(Boc)-Ser(Bu$^t$)-Asp(OBu$^t$)-Gly-Thr(Bu$^t$)-
Phe-Thr(Bu$^t$)-Ser(Bu$^t$)-Glu(OBu$^t$)-Leu-Ser(Bu$^t$)-
Arg(X)-Leu-Arg(X)-Asp(OBu$^t$)-Ser(Bu$^t$)-Ala-
Arg(X)-Leu-Gln-Arg(X)-Leu-Leu-Gln-Gly-Leu-
Val-NH$_2$    [III], in which x is

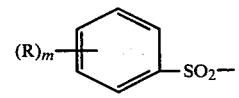

where R is an alkyl or alkoxy having one to the three carbon atoms and m is an integer of 1 to 3, provided that R may be the same or different in case m is 2 or 3. In the formula III, a functional group branched in Arg is defined as above. It is preferred to be tosyl(Tos) or mesitylene-2-sulfonyl(Mts).

As is apparent from the above structural formula, the present invention is characterized in that the imidazole group of histidine is protected by Boc, side chain functional groups of aspartic acid and glutamic acid are protected by OBu$^t$, side chain functional groups of serine and threonine are protected by Bu$^t$ and side chain functional groups of arginine are protected by the group defined as above, such as Tos and Mts, and thus, N-terminal amino groups of secretin and all of side chain functional groups of constituent amino acids are protected. This selection of the protective groups is characterized in that arginine side chains of the insufficient protonation type are protected by the group defined as above such as Tos and Mts and imidazole groups of histidine which are said to cause an undesirable side reaction such as racemization [see Rec. Trav. Chim. Pays. Bas., 93, 256 (1974) and Bull. Chem. Soc. Japan, 51, 3409 (1978)] are protected by tertiary butyloxycarbonyl (Boc) groups. M. Bodanszky et al., Yanaihara et al. and H. C. Beyerman et al. use nitro groups for protection of the former (arginine), and in the process disclosed in Japanese Patent Application Laid-Open Specification No. 12516/77 does not use any protective groups for arginine.

In the conventional processes for the synthesis of secretin, the combination of the protective groups used in the present invention is not adopted at all. In the present invention, by selecting this combination of the protective groups, there can be attained great advantages. Namely, the protective groups can easily be removed at a low temperature in a short time by a simple operation, and high-activity and high-purity secretin can easily be obtained by a simple purification operation.

In the present invention, all the protective groups of the protected secretin [III] can easily be removed at a low temperature in a short time by using a strong acid such as trifluoromethane sulfonic acid and hydrogen fluoride.

Accordingly, the protected secretin [III], that is, the intended heptacosapeptide of the present invention, is very valuable.

In the present invention, if the crude secretin obtained by removing the protective groups by the above-mentioned method is purified, high-activity and high-purity secretin can be obtained.

According to the present invention, high-activity and high-purity secretin can be prepared in a high yield, as described above. The main cause is that the protected secretin [III] is particularly selected as the protected secretin. More specifically, according to the present invention, a protected secretin, in which formation of impurities that can hardly be separated is controlled as much as possible, is synthesized by protecting all the side chain functional groups having a possibility to cause side reactions and after the protective groups are removed from this protected secretin, high-purity and high-activity synthetic secretin can be obtained in a high yield without deactivation loss only by a very simple purification operation.

In the present invention, purification of secretin can be accomplished according to a very simple method as described below. Also in this point, the present invention is very advantageous from the industrial viewpoint.

More specifically, according to the present invention, high-activity and high-purity secretin can be obtained in a high yield by removing all the protective groups from the above-mentioned protected secretin by a strong acid such as trifluoromethane sulfonic acid and hydrogen fluoride (HF), converting the resulting product to an acetate by using an ion exchange resin and subjecting the acetate to column chromatography by gradient elution using ammonium acetate solutions differing in the concentration according to customary procedures using carboxymethyl cellulose. Good results can be obtained if the column chromatography is conducted only once.

Secretin can be obtained in a yield of about 66–73% from the protected secretin according to the above-mentioned purification method. The so obtained secretin has a secretin activity of about 4500–4600 cu/mg, a peptide content of 86–87% as determined by the amino acid analysis and a dry free base activity of about 5200–5300 cu/mg. Accordingly, it is apparent that the secretin obtained according to the present invention has much higher activity and purity than the product obtained according to the above-mentioned process disclosed in Japanese Patent Application Laid-Open Specification No. 12516/77.

In case of a substance which is synthesized through scores of steps and hence expensive and is expected to exert a pharmacological effect with a small amount (10 to 15 cu/man at one administration), such as secretin, drastic improvements of the purity, activity and yield at the final step of the synthesis process is of very great industrial significance, and therefore, the present invention makes great contributions to the art.

Various processes may be considered for production of the protected secretin of the present invention. The processes adopted by us for the synthesis will now be described.

In the structural formula [I] of the protected secretin, the constituent amino acids are numbered from the left N terminal. In principle, the protected peptide of amino acids 1 through 10 as the fragment A, that is, Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-OH, the protected peptide of amino acids 11 through 17 as the fragment B, that is, Z-Ser(Bu$^t$)-Arg(X)-Leu-Arg(X)-Asp(OBu$^t$)-Ser(Bu$^t$)-Ala-OH, and the protected peptide of amino acids 18 through 27 as the fragment C, that is, Z-Arg(X)-Leu-Gln-Arg(X)-Leu-Leu-Gln-Gly-Leu-Val-NH$_2$, are independently synthesized, the fragment B is condensed with the fragment C to form a protected peptide of amino acids 11 through 27 (fragment D), and the protected secretin [III] of the present invention is synthesized by condensing the above protected peptide D with the fragment A. Each of these fragments A, B, C and D is a novel peptide.

In the synthesis of these peptides, since all the side chain functional groups of the respective constituent amino acids are protected, occurrence of undesirable side reactions is remarkably reduced, and these peptides can easily be synthesized according to condensation and purification methods customarily adopted for synthesis of peptides.

In the instant specification, the following abbreviations ordinarily adopted in the field of chemistry of peptides are used.
His: histidine
Ser: serine
Asp: aspartic acid Gly: glycine
Thr: threonine
Phe: phenylalanine
Glu: glutamic acid
Leu: leucine
Arg: arginine
Ala: alanine
Gln: glutamine
Val: valine
Boc: tertiary butyloxycarbonyl
Bu$^t$: tertiary butyl
OBu$^t$: tertiary butyl ester
Tos: tosyl
Mts: mesitylene-2-sulfonyl
Z: benzyloxycarbonyl
DMF: dimethylformamide
ONP: 4-nitrophenyl ester
OSu: N-hydroxysuccinimide ester
OBzl: benzyl ester The present invention will now be described in detail with reference to the following Examples and Referential Examples that by no means limit the scope of the invention.

EXAMPLE 1

Synthesis of Z-Gln-Arg(Tos)-Leu-OH

In 100 ml of dimethylformamide is dissolved 11.4 g (40.7 millimoles) of Z-Gln-OH, and the solution is cooled to $-5°$ C. and 38.7 ml of ethyl chloroformate is added thereto. Under agitation, 4.46 ml of N-methylmorpholine is added to the mixture, and after 15 minutes, 100 ml of a dimethylformamide solution of 16.3 g (37 millimoles) of H-Arg(Tos)-Leu-OH and 4.06 ml of N-methylmorpholine is dropped to the mixture. The mixture is maintained at the same temperature for 3 hours, and 1.8 l of ice water containing 20 ml of 1 M citric acid is added to the mixture and the formed precipitate is recovered by filtration. The precipitate is dissolved in a methanol-ethyl acetate mixed solvent and is re-precipitated by ether. This procedure is repeated 2 times to obtain 18.7 g of a white powder (the yield being 71.9%).

Melting Point:
127.5°–130° C. (decomposition)
TLC:
Rf value=0.62 (butanol/acetic acid/water=4/1/1)
Optical Rotation:
$[\alpha]_D^{25} = -19.5°$ (C=2, methanol)
Elementary Analysis Values as $C_{32}H_{46}N_7O_9S$:
Calculated: C=54.53%, H=6.57%, N=13.91%
Found: C=54.13%, H=6.47%, N=13.65%

EXAMPLE 2

Synthesis of Boc-Leu-Gln-Arg(Tos)-Leu-OH

In 235 ml of N-methylpyrrolidone are dissolved 16.9 g (24 millimoles) of Z-Gln-Arg(Tos)-Leu-OH obtained according to the process of Example 1 and 8.7 g (26.4 millimoles) of Boc-Leu-OSu, and 2.64 ml of N-methylmorpholine is added to the solution. Then, 3 g of 10% Pd-C is added to the mixture, and the mixture is stirred for 5 hours in a current of $H_2$. Then, N-(2-aminoethyl)piperazine is added to the mixture, the mixture is stirred for 1 hour and 100 ml of methanol is added to the mixture. The 10% Pd-C is recoved by filtration, and the mixture is concentrated under reduced pressure to distill N-methylpyrrolidone. The residue is added to a liquid mixture of 100 ml of ethyl acetate and 200 ml of a dilute aqueous solution of citric acid. The mixture is sufficiently stirred, and the ethyl acetate layer is recovered, washed with water, dried and concentrated under reduced pressure. Ether is added to the concentrate and the precipitate is recovered by filtration to obtain 15.6 g of intended Boc-Leu-Gln-Arg(Tos)-Leu-OH (the yield being 83.2%).

Melting point:
138°–141° C. (decomposition)
TLC:
Rf value=0.38 (chloroform/methanol=7/3)
Optical Rotation:
$[\alpha]_D^{25} = -30.6°$ (C=2, methanol)
Elementary Analysis Values as $C_{35}H_{59}N_8O_{10}S \cdot H_2O$:
Calculated: C=52.41%, H=7.67%, N=13.97%
Found: C=52.49%, H=7.45%, N=13.43%

EXAMPLE 3

Synthesis of Z-Arg(Tos)-Leu-Gln-Arg(Tos)-Leu-OH

In 100 ml of dimethylformamide is dissolved 8.3 g (18 millimoles) of Z-Arg(Tos)-OH, and 1.98 ml of N-methylmorpholine is added to the solution. Under cooling to $-10°$ C. and stirring, 1.72 ml of ethyl chloroformate is added to the mixture, and after 5 minutes, 100 ml of a dimethylformamide solution containing 4 ml of N-methylmorpholine and 14.6 g (18 millimoles) of or H-Leu-Gln-Arg(Tos)-Leu-OH.CF$_3$COOH obtained by treating 14.1 g (18 millimoles) of Boc-Leu-Gln-Arg(Tos)-Leu-OH obtained according to the method of Example 2 with a liquid mixture of 50 ml of methylene chloride and 50 ml of trifluoroacetic acid is dropped to the mixture under cooling. The mixture is stirred at $-10°$ C. for 4.5 hours and allowed to stand still in a low temperature chamber overnight, and 0.5 ml of N-(2-aminoethyl)piperazine is added to the mixture and the mixture is stirred at room temperature for 1 hour and added to 1.2 l of a 1% aqueous solution of citric acid. The mixture is sufficiently stirred and the formed precipitate is recovered by filtration, washed with water and dried to obtain 19.4 g of intended Z-Arg(Tos)-Leu-Gln-Arg(Tos)-Leu-OH (the yield being 94%).

Melting Point:
169°–173° C. (decomposition)
TLC:
Rf value=0.23 (chloroform/methanol/acetic acid=85/10/5)
Optical Rotation:
$[\alpha]_D^{25} = -26.0°$ (C=2, methanol)
Elementary Analysis Values as $C_{51}H_{76}N_{12}O_{13}S \cdot H_2O$:
Calculated: C=53.39%, H=6.85%, N=14.65%
Found: C=53.56%, H=6.75%, N=14.72%

EXAMPLE 4

Synthesis of Z-Arg(Tos)-Leu-Leu-Gln-Gly-Leu-Val-NH$_2$

In 300 ml of dimethylformamide is dissolved 37.8 g (81.7 millimoles) of Z-Arg(Tos)-OH, and 8.25 g of N-methylmorpholine is added to the solution. Then, the mixture is cooled to $-5°$ C. and 10.8 g of isobutyl chloroformate is dropped to the mixture over a period of 5 minutes. The mixture is stirred for 15 minutes and mixed with a liquid mixture formed by adding 5.9 g of N-methylmorpholine to a solution of 39.5 g (58.4 millimoles) of HCl.H-Leu-Leu-Gln-Gly-Leu-Val-NH$_2$ [prepared by reducing the Z-compound having a melting point of 261° to 265° C. and an optical rotation $[\alpha]_D^{25}$ of 43.9° (C=2, acetic acid) with equivalent amounts of HCl and trifluoroethanol in the presence of 10% Pd-C] in 400 ml of dimethylformamide. The mixture is stirred at −5° C. for 2.5 hours and added to 3 l of water. The formed precipitate is recovered by filtration, washed with methanol and dissolved in acetic acid, and the solution is added to water. The formed precipitate is recovered by filtration, washed with water and dried to obtain 52.5 g of intended Z-Arg(Tos)-Leu-Leu-Gln-Gly-Leu-Val-$NH_2$ (the yield being 83%).

Melting Point:
248°–254° C.
TLC:
Rf value=0.38 (chloroform/ethanol/acetic acid=80/15/5)
Optical Rotation:
$[\alpha]_D^{25} = -35.2°$ (C=2, acetic acid)
Elementary Analysis Values as $C_{51}H_{80}N_2O_{12}S \cdot \frac{1}{2}H_2O$:
Calculated: C=55.08%, H=7.47%, N=15.12%
Found: C=55.13%, H=7.43%, N=14.79%

EXAMPLE 5

Synthesis of Z-Gln-Arg(Tos)-Leu-Leu-Gln-Gly-Leu-Val-$NH_2$

In a mixed liquid of 100 ml of acetic acid, 100 ml of 25% HBR-acetic acid and 3.4 g of anisole is dissolved 33.5 g (30.9 millimoles) of Z-Arg(Tos)-Leu-Leu-Gln-Gly-Leu-Val-$NH_2$, and the solution is stirred at room temperature for 1.5 hours and is then added to 2.5 l of ether. The formed precipitate is recovered by decantation and dissolved in 300 ml of ethanol. The solution is added to ether and an HBr salt of the Z-compound is recovered by decantation. Then, the recovered salt (34.5 g, 30.9 millimoles) is dissolved in 400 ml of dimethylformamide, and 6.8 g of N-methylmorpholine is added to the solution under cooling. Then, 14 g (37 millimoles) of crystalline Z-Gln-OSu is added to the mixture, and the mixture is stirred at −5° C. for 2 hours and allowed to stand at room temperature for 2 days. Then, 2 g of N-(2-aminoethylpiperazine) is added to the reaction mixture, and the mixture is stirred for 30 minutes and added to 2.5 l of 1 N HCl. The formed precipitate is recovered by filtration, washed with water, suspended in 400 ml of methanol, stirred and recovered by filtration to obtain 31.5 g of intended Z-Gln-Arg(Tos)-Leu-Leu-Gln-Gly-Leu-Val-$NH_2$ (the yield being 84.2%).

Melting Point:
265°–269° C. (decomposition)
TLC:
Rf value=0.35 (chloroform/methanol=4/1)
Optical Rotation:
$[\alpha]_D^{26} = -39.9°$ (C=2, acetic acid)
Elementary Analysis Values as $C_{56}H_{88}N_{14}O_{14}S \cdot H_2O$:
Calculated: C=54.63%, H=7.31%, N=15.93%
Found: C=54.43%, H=7.22%, N=15.74%

EXAMPLE 6

Synthesis of Boc-Leu-Gln-Arg(Tos)-Leu-Leu-Gln-Gly-Leu-Val-$NH_2$

In 400 ml of N-methylpyrrolidone is dissolved 28 g (23 millimoles) of Z-Gln-Arg(Tos)-Leu-Leu-Gln-Gly-Leu-Val-$NH_2$, and 3 g of 10% Pd-C and 8.32 g (25.4 millimoles) of Boc-Leu-OSu are added to the solution and the mixture is stirred in a current of $H_2$ for 8 hours. Supply of $H_2$ is stopped and the vessel is closed, and the reaction mixture is allowed to stand at room temperature overnight. The catalyst is removed by filtration, and the filtrate is concentrated under reduced pressure. When the volume is reduced to about 80 ml, 100 ml of methanol and 200 ml of water are added to the concentrate. The precipitated oily substance is recovered by decantation, and 500 ml of water is further added to the oily substance to solidify it. The solid is recovered by filtration, washed with water and dried to obtain 27.2 g (the yield being 92.2%) of intended Boc-Leu-Gln-Arg(Tos)-Leu-Leu-Gln-Gly-Leu-Val-$NH_2$.

Melting Point:
255°–256° C.
TLC:
Rf value=0.48 (chloroform/methanol/acetic acid=80/15/5)
Optical Rotation:
$[\alpha]_D^{26} = -42.3°$ (C=2, acetic acid)
Elementary Analysis Values as $C_{59}H_{101}N_{15}O_{15}S \cdot 2H_2O$:
Calculated: C=54.00%, H=8.00%, N=16.01%
Found: C=53.69%, H=7.83%, N=15.69%

EXAMPLE 7

Synthesis of Z-Arg(Tos)-Leu-Gln-Arg(Tos)-Leu-Leu-Gln-Gly-Leu-Val-$NH_2$

Process (1)

Trifluoroacetic acid is added to 27.1 g of Boc-Leu-Gln-Arg(Tos)-Leu-Leu-Gln-Gly-Leu-Val-$NH_2$ obtained in Example 6, and reaction is conducted for 1 hour. The reaction mixture is concentrated under reduced pressure and ether is added to the residue. Then, 28 g (21.7 millimoles) of the so obtained trifluoroacetic acid salt of the Boc-free compound is dissolved in 350 ml of dimethylformamide, and the solution is cooled and 3.44 ml of N-methylmorpholine is added thereto. Then, the mixture is cooled to −10° C. and 3.84 ml of isobutyl chloroformate is added to the mixture. After 10 minutes, the solution is stirred for 2.5 hours at the same temperature. Then, the temperature is elevated to room temperature, and 15 ml of a 2 M aqueous solution of $KHCO_3$ is added to the solution and the mixture is stirred for 30 minutes and added to 1.5 l of ice water. The formed precipitate is recovered by filtration and dissolved in 300 ml of hot methanol, and insoluble substances are removed by filtration and the filtrate is concentrated under reduced pressure. Then, ethyl acetate is added to the residue to obtain 27.5 g of intended Z-Arg(Tos)-Leu-Gln-Arg(Tos)-Leu-Leu-Gln-Gly-Leu-Val-$NH_2$ (the yield being 80%).

Melting point:
235°–250° C. (decomposition)
TLC:
Rf value=0.41 (chloroform/methanol/acetic acid=80/15/5)
Optical Rotation:
$[\alpha]_D^{28} = -31.8°$ (C=2, acetic acid)
Elementary Analysis Values as $C_{75}H_{117}N_{19}O_{18}S_2 \cdot 2H_2O$:
Calculated: C=53.9%, H=7.05%, N=15.47%
Found: C=53.84%, H=7.29%, N=15.90%

Process (2)

In 100 ml of dimethylformamide are dissolved 5.35 g (4.75 millimoles) of Z-Arg(Tos)-Leu-Gln-Arg(Tos)-Leu-OH obtained in Example 3 [having a melting point of 169° to 173° C. and an optical rotation $[\alpha]_D^{25}$ of −26.0° (C=2, methanol)] and 0.55 g of N-hydroxysuccinimide. The solution is cooled to 0° C. and 0.98 g of dicyclohexylcarbodiimide is added, and the mixture is stirred for 3 hours and further stirred in a low temperature chamber (2° to 3° C.) for 1.5 days. Separately, 3.05 g (4.75 millimoles) of $CF_3COOH.H$-Leu-Gln-Gly-Leu-Val-$NH_2$ [obtained by treating Boc-Leu-Gln-Gly-Leu-Val-$NH_2$ having a melting point of 236° to 238° C. and an optical rotation $[\alpha]_D^{20}$ cf $-18.9°$ (C=2, DMF), with $CF_3COOH$] is dissolved in 50 ml of DMF and 0.52 ml of N-methylmorpholine is added, and the solution is cooled to 0° C. and added to the above mixture. The resulting mixture is stirred for 1 day in a low temperature chamber and for 2 days at room temperature. The formed precipitate is removed by filtration, and the filtrate is concentrated under reduced pressure and added to 300 ml of a 2% aqueous solution of sodium bicarbonate. The formed precipitate is recovered by filtration to obtain 7.7 g of intended Z-Arg(Tos)-Leu-Gln-Arg(Tos)-Leu-Leu-Gln-Gly-Leu-Val-$NH_2$ having the same properties as those of the compound obtained according to the above preparation process (1).

EXAMPLE 8

Synthesis of H-Arg(Tos)-Leu-OH
(i) Synthesis of Z-Arg(Tos)-Leu-OBzl

In 500 ml of tetrahydrofuran is dissolved 46.2 g (100 millimoles) of Z-Arg(Tos)-OH, and 11 ml of N-methylmorpholine is added to the solution and the mixture is stirred at $-5°$ C. for 5 minutes. Then, 9.6 ml of ethyl chloroformate is added to the mixture, and a cooled solution of 39.4 g (100 millimoles) of Tos-OH.H-Leu-OBzl and 11 ml of N-methylmorpholine in dimethylformamide is added to the above mixture. The resulting mixture is stirred at $-5°$ to 0° C. for 4 hours and concentrated under reduced pressure. The residue is dissolved in 700 ml of ethyl acetate, and the solution is washed with 0.1 N aqueous hydrochloric acid, 1 N aqueous $NaHCO_3$ and water and concentrated under reduced pressure. Ether is added to the residue and the formed precipitate is recovered by filtration to obtain 58 g of intended Z-Arg(Tos)-Leu-OBzl (the yield being 87%).
 Melting Point:
 142°–143.5° C. (decomposition)
 TLC:
 Rf value=0.59 (chloroform/methanol=9/1)
 Elementary Analysis Values as $C_{34}H_{43}N_5O_7S$:
  Calculated: C=61.34%, H=6.51%, N=10.52%
 Found: C=61.58%, H=6.58%, N=10.45%
 (ii) Synthesis of H-Arg(Tos)-Leu-OH In a liquid mixture of 800 ml of methanol and 100 ml of water is suspended 55 g of Z-Arg(Tos)-Leu-OBzl obtained according to the process (i), and the suspension is stirred for 7 hours in the presence of 3 g of 10% Pd-C in a current of $H_2$. The catalyst is removed by filtration, and the filtrate is concentrated under reduced pressure. Ether is added to the residue to recover 37.5 g of intended H-Zrg(Tos)-Leu-OH.
 Melting Point:
 137°–145° C. (decomposition)
 TLC:
 Rf value=0.73 (butanol/acetic acid/water=4/1/5)
 Optical Rotation:
 $[\alpha]_D^{25}=+9.4°$ (C=2, methanol)
 Elementary Analysis Values as $C_{19}H_{31}N_5O_5S.H_2O$:
  Calculated: C=49.66%, H=7.23%, N=15.24%
 Found: C=50.00%, H=7.04%, N=15.20%

EXAMPLE 9

Synthesis of Z-Ser($Bu^t$)-Arg(Tos)-Leu-OH

In 250 ml of tetrahydrofuran are dissolved 23.7 g (80.4 millimoles) of Z-Ser($Bu^t$)-OH and 10.2 g of N-hydroxysuccinimide, and the solution is cooled to 0° C. and 16.6 g of dicyclohexylcarbodiimide is added to the solution. The mixture is stirred for 3 hours at the above temperature and then stirred in a low temperature chamber overnight. The formed precipitate is removed by filtration and the filtrate is concentrated under reduced pressure. The obtained oily substance is dissolved in 100 ml of dimethylformamide. This solution is mixed with a solution formed by dissolving 35.5 g (80.4 millimoles) of H-Arg(Tos)-Leu-OH prepared according to the process (ii) of Example 8 in 200 ml of dimethylformamide and adding 11.2 ml of triethylamine to the solution, and the mixture is stirred for 6 hours at 6° C., overnight in a low temperature chamber and for 5 hours at room temperature. The insoluble substances are removed by filtration and the filtrate is concentrated under reduced pressure. The residue is extracted with 700 ml of ethyl acetate, washed with 2% citric acid and water and dried with magnesium sulfate. The dried filtrate is concentrated under reduced pressure and ether is added to the residue to effect solidification. The solid is dissolved in a mixed liquid of chloroform and methanol, and the solution is concentrated under reduced pressure. Solidification is effected by ethyl acetate to obtain 41.9 g of intended Z-Ser($Bu^t$)-Arg(Tos)-Leu-OH (the yield being 73%).
 Melting Point:
 175°–177.5° C. (decomposition)
 TLC:
 Rf value=0.61 (chloroform/methanol=3/1)
 Optical Rotation:
 $[\alpha]_D^{27}=-10.9°$ (C=2, methanol)
 Elementary Analysis Values as $C_{34}H_{50}N_6O_8S.H_2O$:
  Calculated: C=56.65%, H=7.27%, N=11.66%
 Found: C=56.62%, H=7.09%, N=11.62%

EXAMPLE 10

Synthesis of Z-Arg(Tos)-Asp($OBu^t$)-Ser($Bu^t$)-Ala-OH

In 290 ml of dimethylformamide is dissolved 16.2 g (35 millimoles) of Z-Arg(Tos)-OH, and 3.85 ml of N-methylmorpholine is added to the solution and the mixture is cooled to $-5°$ C. Then, 3.35 ml of ethyl chloroformate is dropped to the mixture under agitation and the mixture is stirred for 15 minutes and is then mixed with a cooled liquid formed by suspending 15.5 g (38.5 millimoles) of H-Asp($OBu^t$)-Ser($Bu^t$)-Ala-OH (having a melting point of 122° to 133° C.) in 290 ml of dimethylformamide and adding 4.3 ml of N-methylmorpholine. The resulting mixture is stirred for 3 hours, and the insoluble substances are removed by filtration. The filtrate is concentrated under reduced pressure and solidification is effects by addition of ether to obtain 26.6 g of intended glassy Z-Arg(Tos)-Asp($OBu^t$)-Ser($Bu^t$)-Ala-OH (the yield being 90%).
 TLC:
 Rf value=0.51 (chloroform/methanol=4/1)
 Optical Rotation:
 $[\alpha]_D^{26}=-9.9°$ (C=2, methanol)
 Elementary Analysis Value as $C_{39}H_{57}N_7O_{12}S$:
  Calculated: C=55.24%, H=6.78%, N=11.56%
 Found: C=55.08%, H=7.10%, N=11.56%

EXAMPLE 11

Synthesis of Z-Ser(Bu$^t$)-Arg(Tos)-Leu-Arg(Tos)-Asp(OBu$^t$)-Ser(Bu$^t$)-Ala-OH In 90 ml of dimethylformamide are dissolved 20.3 g (28.2 millimoles) of Z-Ser(Bu$^t$)-Arg(Tos)-Leu-OH and 3.57 g of N-hydroxysuccinimide, and the solution is cooled to $-5°$ C. and 5.8 g of dicyclohexylcarbodiimide is added to the solution under agitation. The mixture is stirred at $-5°$ C. for 3 hours and allowed to stand still in a low temperature chamber overnight. Separately, 25 g of Z-Arg(Tos)-Asp(OBu$^t$)-Ser(Bu$^t$)-Ala-OH obtained according to the method of Example 10 is reacted in the presence of 10% Pd-C in 80% trifluoroethanol in a current of H$_2$ for 6 hours, and 21 g (28 millimoles) of the resulting Z-free derivative of the above compound is suspended in 110 ml of dimethylformamide. Then, 3.1 ml of N-methylmorpholine is added to the suspension and the mixture is stirred and cooled.

The mixture is then added to the above liquid reaction mixture, and the resulting mixture is stirred at 0° C. for 6 hours, allowed to stand in a low temperature chamber overnight and then stirred at 0° C. for 6 hours. The formed precipitate is separated by filtration, and the filtrate is concentrated under reduced pressure and the residue is added to 400 ml of 0.05 M citric acid. The formed precipitate is recovered by filtration, washed with water and dissolved in a mixed liquid of trifluoroethanol, methanol and chloroform. The solution is concentrated under reduced pressure and ethyl acetate is added to the concentrate, and the formed precipitate is recovered by filtration to obtain 29.1 g of intended Z-Ser(Bu$^t$)-Arg(Tos)-Leu-Arg(Tos)-Asp(OBu$^t$)-Ser(Bu$^t$)-Ala-OH (the yield being 73%).

Melting Point:
164° C. (decomposition)
TLC:
Rf value=0.57 (chloroform/methanol=7/2)
Optical Rotation:
$[\alpha]_D^{22} = -11.6°$ (C=2, trifluoroethanol)
Elementary Analysis Values as $C_{65}H_{99}N_{13}O_{18}S_2$:
  Calculated: C=55.18%, H=7.05%, N=12.87%
Found: C=54.96%, H=7.21%, N=12.75%

EXAMPLE 12

Synthesis of Z-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ In 1.65 ml of 1% N-methylmorpholine/dimethylformamide are dissolved 127 mg (0.15 millimole) of Z-Arg(Tos)-Asp(OBu$^t$)-Ser(Bu$^t$)-Ala-OH and 231 mg (0.15 millimole) of HCl.H-Arg(Tos)-Leu-Gln-Arg(Tos)-Leu-Leu-Gln-Gly-Leu-Val-NH$_2$, and 2.43 ml of 1% N-hydroxybenxtriazole/dimethylformamide is added to the solution and 1.63 ml of 2% dicyclohexylcarbodiimide/dimethylformamide is further added under cooling by sodium chloride/ice. The mixture is stirred at 0° C. for 1 hour and in a low temperature room for 2 days. The mixture is added to 50 ml of 2% aqueous citric acid, and the formed precipitate is recovered by filtration and washed with water and 2% aqueous NaHCO$_3$ to obtain 298 mg of Z-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$.

Melting Point:
222°–226° C. (decomposition)
TLC:
Rf value=0.60 (chloroform/methanol=4/1)
Optical Rotation:
$[\alpha]_D^{25} = -20.2°$ (C=2, trifluoroethanol)
Elementary Analysis Values as $C_{107}H_{166}N_{26}O_{27}S_3$:
  Calculated: C=54.80%, H=7.15%, N=15.53%
Found: C=54.65%, H=7.14%, N=15.35%

The above mentioned Z-free derivative will be illustrated in respect to the preparation and its physical properties.

HCl.H-Arg(Tos)-Leu-Gln-Arg(Tos)-Leu-Leu-Gln-Gly-Leu-Val-NH$_2$ 12.0 g (7.33 millimoles) of Z-Arg(Tos)-Leu-Gln-Arg(Tos)-Leu-Leu-Gln-Gly-Leu-Val-NH$_2$ was dissolved in 180 ml of an aqueous 80% acetic acid solution. Then hydrogen gas was introduced into the resulting solution over a period of 12 hours, while agitated, in the presence of 1.2 g of 10% Pd-C. The Pd-C was filtrated out and 8.8 ml of 1 N-HCl solution was added to the resulting filtrate. The mixture was concentrated under a reduced pressure and the residue was dissolved in trifluoroethanol. The solution was treated by filtration and concentrated. Ether was added to the residue and the produced precipitate was separated by filtration. In this was 10.9 g (yield 97%) of HCl.H-Arg(Tos)-Leu-Gln-Arg(Tos)-Leu-Leu-Gln-Gly-Leu-Val-NH$_2$.

Physical properties thereof are:
Melting Point:
172°–176° C. (decomposed)
TLC:
Rf value=0.51 (butanol/acetic acid/water=4/1/1)
Optical Reaction:
$[\alpha]_D^{30} = -33.3°$ (C=1, acetic acid)
Elementary Analysis Values as $C_{67}H_{111}N_{19}O_{16}S_2.HCl.3/2CF_3CH_2OH$
  Calculated: C=49.76%, H=6.95%, N=15.75%
Found: C=49.67%, H=7.12%, N=16.04%

EXAMPLE 13

Synthesis of Z-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ Preparation Process (1):

To 130 ml of dimethylformamide is added 1.15 g of N-hydroxysuccinimide, and 10.12 g (7.2 millimoles) of Z-Ser(Bu$^t$)-Arg(Tos)-Leu-Arg(Tos)-Asp(OBu$^t$)-Ser(Bu$^t$)-Ala-OH is dissolved therein. Then, 11.0 g (7.2 millimoles) of HCl.H-Arg(Tos)-Leu-Gln-Arg(Tos)-Leu-Leu-Gln-Gly-Leu-Val-NH$_2$ obtained by reducing 12.0 g of the Z-compound obtained according to the method of Example 7 in the presence of 10% Pd-C in 80% acetic acid and converting the reduction product to a hydrochloride is added to the solution, and 7.2 ml of a dimethylformamide (DMF) solution of N-methylmorpholine (1 millimole per ml of DMF) is further added. The mixture is cooled to $-10°$ C. and a dimethylformamide solution containing 1.62 g of dicyclohexylcarbodiimide is added to the mixture under agitation. Reaction is conducted for 3 hours, and the mixture is stirred in a low temperature (4° C.) for 2.5 days and at room temperature for 1 day. The mixture is concentrated under reduced pressure, and the residue is added to 800 ml of a 2% aqueous solution of sodium bicarbonate. The formed precipitate is recovered by filtration, washed with 200 ml of a dilute solution of sodium bicarbonate and 200 ml of water and treated with chloroform/methanol/ether to obtain 13.4 g of intended Z-Ser(Bu$^t$)-Arg(Tos)-Leu-Arg(Tos)-Asp(OBu$^t$)-Ser(Bu$^t$)-

Ala-Arg(Tos)-Leu-Gln-Arg(Tos)-Leu-Leu-Gln-Gly-Leu-Val-NH$_2$ (the yield being 64.6%).

Melting Point:
236° C. (decomposition)
TLC:
Rf value=0.65 (chloroform/methanol=3/1)
Optical Rotation:
[α]$_D^{27}$= −10.5° (C=1, trifluoroethanol)
Elementary Analysis Values as C$_{132}$H$_{208}$N$_{32}$O$_{33}$S$_4$:
Calculated: C=54.67%, H=7.23%, N=15.45%
Found: C=54.19%, H=7.39%, N=15.30%

Preparation Process (2):

In 20 ml of 80% acetic acid is dissolved 600 mg (0.257 millimole) of Z-Arg(Tos)-Asp(OBu')-Ser(Bu')-Ala-Arg(Tos)-Leu-Gln-Arg(Tos)-Leu-Leu-Gln-Gly-Leu-Val-NH$_2$ obtained according to the method of Example 12, and the solution is stirred in the presence of 10% Pd-C in a current of H$_2$ to effect Z-removing reaction. Then 0.257 ml of an equivalent amount of N-HCl is added to the reaction mixture. The catalyst is removed by filtration and the reaction product is treated with ether to obtain 501 mg of the hydrochloride of the Z-free compound (the yield being 83.5%).

In a mixed liquid of 8 ml of dimethylformamide and 2.37 ml of 1% N-methylmorpholine/dimethylformamide are dissolved 460 mg (0.205 millimole) of the so obtained hydrochloride and 147 mg (10.205 millimoles) of Z-Ser(Bu')-Arg(Tos)-Leu-OH obtained according to the method of Example 9. Then, 1.66 ml of 2% N-hydroxybenztriazole/dimethylformamide is added to the solution, and 2.32 ml of 2% dicyclohexylcarbodiimide/dimethylformamide is further added under cooling and agitation. Reaction is carried out at 0° C. for 1 hour under agitation, and the reaction mixture is allowed to stand in a low temperature chamber for 2 days. The formed precipitate is removed by filtration, and the filtrate is concentrated under reduced pressure. Then, 50 ml of 2% aqueous NaHCO$_3$ is added to the residue, and the formed precipitate is recovered by filtration, washed with water, dried and treated with chloroform/methanol to obtain 317 mg of intended Z-Ser(Bu')-Arg(Tos)-Leu-Arg(Tos)-Asp(OBu')-Ser(-Bu')-Ala-Arg(Tos)-Leu-Gln-Arg(Tos)-Leu-Leu-Gln-Gly-Leu-Val-NH$_2$ (the yield being 53.4%) having the same properties as those of the product obtained according to the above-mentioned preparation process (1).

EXAMPLE 14

Synthesis of Z-Ser(Bu')-Asp(OBu')-Gly-Thr(Bu')-Phe-Thr(Bu')-Ser(Bu')-Glu(OBu')-Leu-OH In 120 ml of dimethylformamide is dissolved 18.13 g (21.9 millimoles) of Z-Ser(Bu')-Asp(OBu')-Gly-Thr(Bu')-Phe-OH, and at 0° C., 2.52 g of N-hydroxysuccinimide and 4.51 g of dicyclohexylcarbodiimide are added to the solution. At the same temperature, the mixture is stirred for 3 hours, and the mixture is allowed to stand in a low temperature chamber overnight. Then, the mixture is further stirred at room temperature for 3 hours and the formed precipitate is recoved by filtration. Separately, Z-Thr(Bu')-Ser(Bu')-Gln(OBu')-Leu-OH is subjected to catalytic reduction in the presence of 10% Pd-C in methanol to remove the group Z. Then, 13.5 g (21.9 millimoles) of the so obtained H-Thr(Bu')-Ser(Bu')-Glu(OBu')-Leu-OH is suspended in a liquid mixture of 80 ml of dimethylformamide and 20 ml of N-methylpyrrolidone, and 2.65 ml of N-methylmorpholine is added to the suspension and the mixture is stirred for 1 hour.

The mixture is mixed with the above filtrate at 0° C., and the resulting mixture is stirred for 3 hours to obtain a transparent solution. The solution is allowed to stand still in a low temperature chamber overnight and poured into a 1/20 M aqueous solution of citric acid, and the formed precipitate is recovered by filtration, washed with water and dried to obtain 27.0 g of intended Z-Ser(Bu')-Asp(OBu')-Gly-Thr(Bu')-Phe-Thr(Bu')-Ser(Bu')-Glu(OBu')-Leu-OH (the yield being 87%).

Melting Point:
242° C. (decomposition)
TLC:
Rf value=0.38 (chloroform/methanol=9/1)
Optical Rotation:
[α]$_D^{24}$= +7.1° (C=1.6, chloroform/methanol=2/1)
Elementary Analysis Values as C$_{72}$H$_{115}$N$_9$O$_{20}$:
Calculated: C=60.60%, H=8.14%, N=8.84%
Found: C=60.59%, H=8.39%, N=9.09%

EXAMPLE 15

Synthesis of Boc-His(Boc)-Ser(Bu')-Asp(OBu')-Gly-Thr(Bu')-Phe-Thr(Bu')-Ser(Bu')-Glu(OBu')-Leu-OH In 150 ml of 80% trifluoroethanol is dissolved 15 g (10.5 millimoles) of Z-Ser(Bu')-Asp(OBu')-Gly-Thr(Bu')-Phe-Thr(Bu')-Ser(Bu')-Glu(OBu')-Leu-OH obtained according to the method of Example 14, and the solution is stirred for 10 hours in the presence of 2.4 g of 10% Pd-C in a current of H$_2$. The precipitated crystal is dissolved in 200 ml of chloroform, and the catalyst is removed by filtration and the filtrate is concentrated under reduced pressure. Then, 70 ml of ether is added to the residue and the precipitated crystal is recovered by filtration to obtain 13.4 g of the Z-free derivative of the above compound (the yield being 89.5%). Then, 11.0 g (8.51 millimoles) of the obtained Z-free derivative is dissolved in 250 ml of N-methylpyrrolidone, and 8.51 ml of an N-methylmorpholine/dimethylformamide (DMF) solution (1 millimole per ml of DMF) is added to the solution. After 5 minutes, 4.9 g of Boc-His(Boc)-ONP is added to the mixture, and the resulting mixture is stirred at 40° C. for 44 hours. The liquid reaction mixture is added to a mixed liquid of 700 ml of cold water containing 0.515 g of acetic acid and 70 ml of ether. The formed precipitate is recovered by filtration, washed with water and ether and purified with trifluoromethanol/methanol to obtain 12.1 g of intended Boc-His(Boc)-Ser(Bu')-Asp(OBu')-Gly-Thr(Bu')-Phe-Thr(Bu')-Ser(Bu')-Glu(OBu')-Leu-OH (the yield being 87.3%).

Melting Point:
234° C. (decomposition)
TLC:
Rf value=0.43 (chloroform/methanol=10/1)
Optical Rotation:
[α]$_D^{25}$= −0.78° (C=2, trifluoroethanol)
Elementary Analysis Values as C$_{80}$H$_{132}$N$_{12}$O$_{23}$:
Calculated: C=58.95%, H=8.16%, N=10.31%
Found: C=58.76%, H=8.37%, N=10.18%

EXAMPLE 16

Synthesis of Z-Ser(Bu')-Asp(OBu')-Gly-Thr(Bu')-Phe-Thr(Bu')-Ser(Bu')-Glu(OBu')-Leu-Ser(Bu')-Arg(Tos)-Leu-Arg(Tos)-Asp(OBu')-Ser(Bu')-Ala- Arg(Tos)-Leu-Gln-Arg(Tos)-Leu-Leu-Gln-Gly-Leu-Val-NH$_2$ To 32 ml of N-methylpyrrolidone are added 509 mg (0.36 millimoles) of Z-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-OH, 1000 mg (10.36 millimole) HCl.H-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ obtained according to the method of Example 14 (Z is removed from the Z-compound obtained according to the method of Example 13 in the presence of Pd-C in 80% acetic acid by H$_2$ and the Z-free compound is converted to a hydrochloride) and 58 mg of N-hydroxybenztriazole, and 3.57 ml of a dimethylformamide (DMF) solution containing 0.1 millimole of N-methylmorpholine (NMM) per ml of DMF is further added. Then, 88.3 g of dicyclohexylcarbodiimide is added to the resulting solution at 0° C. The solution is stirred for 5 hours at 0° C. and for two days and nights at room temperature. Then, the reaction mixture is concentrated under reduced pressure until the volume is reduced to ½. The concentrate is poured into 200 ml of ice water, and the formed precipitate is recovered by filtration and treated with methanol to obtain 990 mg of intended Z-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ (the yield being 66%).

Melting Point:
238° C. (decomposition)
TLC:
Rf value=0.59 (chloroform/methanol=3/1)
Optical Rotation:
$[\alpha]_D^{24} = -7.75°$ (C=2, trifluoroethanol)
Elementary Analysis Values as C$_{196}$H$_{315}$N$_{41}$O$_{50}$S$_4$.3CF$_3$.CH$_2$OH:
Calculated: C=54.21%, H=7.31%, N=12.81%
Found: C=54.36%, H=7.40%, N=13.10%

EXAMPLE 17

Synthesis of Protected Secretin, Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ Preparation Process (1):

In a mixed liquid of 85 ml of dimethylformamide and 85 ml of N-methylpyrrolidone are dissolved 3.49 g (2.14 millimoles) of Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-OH, 5 g (1.78 millimoles) HCl.H-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ obtained according to the method of Example 15 (Z is removed from the Z-compound obtained according to the method of Example 13 in presence of 10% Pd-C in 80% acetic acid by H$_2$ and the resulting Z-free compound is converted to a hydrochloride) and 0.345 g of N-hydroxysuccinimide. The solution is cooled and 1.87 ml of a dimethylformamide solution containing 1 millimole of N-methylmorpholine per ml of DMF is added to the solution. Then, 0.529 g of dicyclohexylcarbodiimide is added to the solution, and the solution is stirred in an ice chamber for 1 day and reaction is then carried out at room temperature for 3 days. The reaction mixture is added to a liquid mixture of water and ether, and the formed precipitate is recovered by filtration to obtain 8 g of a crude product of the intended protected secretin, Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$. The crude product is purified by silica gel chromatography (Wako Gel C200, 5.5 cm in diameter and 20 cm in length, elution with chloroform/methanol) to obtain 4.0 g of the intended product (the yield being 52.5%).

Melting Point:
251° C. (decomposition)
TLC:
Single spot, Rf value=0.57 (chloroform/methanol=4/1)
Optical Rotation:
$[\alpha]_D^{23} = -7.36°$ (C=1, trifluoroethanol)
Elementary Analysis Values as C$_{204}$H$_{332}$N$_{44}$O$_{53}$S$_4$.5H$_2$O:
Calculated: C=54.83%, H=7.71%, N=13.79%
Found: C=54.90%, H=7.73%, N=13.74%

Preparation Process (2):

In a liquid mixture of 20 ml of trifluorethanol and 10 ml of 80% acetic acid is dissolved 250 ml (0.06 millimole) of Z-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ obtained according to the method of Example 16, and 150 mg of 10% Pd-C is added to the solution and the solution is stirred for 6 hours in a current of H$_2$. The catalyst is removed by filtration, and the filtrate is concentrated under reduced pressure. Then, 60 ml of ether is added to the concentrate, and the formed precipitate is recovered by filtration and dried to obtain 321 ml of the Z-free derivative of the intended compound (the yield being 93%).

In 5 ml of dimethylformamide is dissolved 204 mg (0.05 millimole) of the so obtained compound as much as possible, and 71 mg (0.15 millimole) of Boc-His(Boc)-ONP is added to the solution and 0.5 ml of a dimethylformamide solution containing 0.1 mole of N-methylmorpholine per ml of DMF is added to the solution. Then, 1 ml of dimethylformamide and 1 ml of N-methylpyrrolidone are further added, and reaction is carried out at room temperature for 3 days under agitation. The liquid reaction mixture is concentrated under reduced pressure and ether is added to the concentrate. The formed precipitate is recovered by filtration and washed with ether to obtain 200 mg of the intended compound having the same properties as those of the compound obtained according to the above preparation process (1).

EXAMPLE 18

Synthesis of Crude Secretin:

In a closed hydrogen fluoride (HF) reaction vessel, 2.32 g of the protected secretin obtained in Example 17 is dissolved in 50 ml of HF in the presence of anisole at −5° C., and the mixture is stirred for 1 hour while distilling HF from the reaction system. The residue is washed with ether, dissolved in cold water and converted to an acetate by treatment with Amberlite IRA-93 (acetic acid type). Then, the acetate is free-dried to obtain 1.53 g of white powdery crude secretin (the yield being 88%).

EXAMPLE 19

Purification of Crude Secretin:

In 50 ml of water is dissolved 587 mg of the crude secretin obtained in Example 18, and the solution is charged in a column (3.2 cm in diameter and 32 cm in length) of carboxymethyl cellulose (Whatman CM-52) and elution is carried out with 0.05 M ammonium acetate and 0.13 M ammonium acetate. Each fraction consists of 210 drops. Good secretin eluate is contained in 122nd to 178th drops in each fraction. The secretin-containing drops are combined and freeze-dried to obtain 441 mg of purified secretin (the yield being 75%). The biological activity of this purified secretin is about 4600 cu/mg, and from the amino acid analysis, it is found that the peptide content is about 87%. By the disc electrophoreiss, thin layer chromatography and high speed liquid chromatography, it is confirmed that the obtained purified product is a single substance.

The purified secretin obtained according to the process of this Example has an activity of 5287 cu/mg as the dry free base, and it is found that the product has a very high activity.

TLC:
Rf value=0.54 (butanol/acetic acid/pyridine/water=15/5/5/8)

Optical Rotation:
$[\alpha]_D^{16} = -57.2°$ (C=0.402, 0.01 N HCl)
$[\alpha]_D^{25} = -49.03°$ (C=1.04, 1 N acetic acid)

Amino Acid Analysis Values:
His 1.02 (1), Arg 4.03 (4), Asp 1.97 (2), Thr 1.87 (2), Ser 4.30 (4), Glu 2.88 (3), Gly 1.97 (2), Ala 1.02 (1), Val 0.93 (1), Leu 6.04 (6), Phe 1.00 (1), peptide content=87%

EXAMPLE 20

Synthesis of Z-Gln-Arg(Mts)-Leu-OH

In 30 ml of dimethylformamide is dissolved 5.6 g (20 millimoles) of Z-Gln-OH, and the solution is cooled to −5° C. and 1.9 ml of ethyl chloroformate is added thereto. Under agitation, 2.2 ml of N-methylmorpholine is added to the mixture, and after 15 minutes, 30 ml of a dimethylformamide solution of 8.0 g (17 millimoles) of H-Arg(Mts)-Leu-OH and 1.9 ml of N-methylmorpholine is dropped to the mixture. The mixture is maintained at the same temperature for 6 hours, and 1.0 l of ice water containing 20 ml of 1 M citric acid is added to the mixture and the formed precipitate is recovered by filtration. The precipitate is dissolved in a methanol-ethyl acetate mixed solvent and is re-precipitated by ether. This procedure is repeated 2 times to obtain 10.4 g of a white powder (the yield being 83.6%).

Melting Point:
126.0°–130° C. (decomposition)

TLC:
Rf value=0.29 (chloroform/methanol=7/4)

Optical Rotation:
$[\alpha]_D^{27} = -19.6°$ (C=1, methanol)

Elementary Analysis as $C_{34}H_{49}N_7O_9S$:
Calculated: C=55.80%, H=6.75%, N=13.40%
Found: C=55.52%, H=7.04%, N=13.70%

EXAMPLE 21

Synthesis of Boc-Leu-Gln-Arg(Mts)-Leu-OH

In 120 ml of dimethylformamide are dissolved 9.5 g (13 millimoles) of Z-Gln-Arg(Mts)-Leu-OH obtained according to the process of Example 20 and 5.2 g (16 millimoles) of Boc-Leu-OSu, and 1.43 ml of N-methylmorpholine is added to the solution. Then 0.5 g of 10% Pd-C is added to the mixture, and the mixture is stirred for 5 hours in a current of $H_2$. The N-(2-aminoethyl)piperazine is added to the mixture, the mixture is stirred for 1 hour. The 10% Pd-C is recovered by filtration, and the mixture is cancentrated under reduced pressure. The residue is added to a liquid mixture of 100 ml of ethyl acetate and 200 ml of a dilute aqueous solution of citric acid. The mixture is sufficiently stirred, and the ethyl acetate layer is recovered, washed with water, dried and concentrated under reduced pressure. Ether is added to the concentrate and the precipitate is recovered by filtration to obtain 9.5 g of intended Boc-Leu-Gln-Arg(Mts)-Leu-OH (the yield being 86.5%).

Melting Point:
140°–146° C. (decomposition)

TLC:
Rf value=0.40 (chloroform/methanol/acetic acid=80/15/5)

Optical Rotation:
$[\alpha]_D^{27} = -27.3°$ (C=1, trifluoroethanol)

Elementary Analysis as $C_{37}H_{62}N_8O_{10}S$:
Calculated: C=54.79%, H=7.71%, N=13.82%
Found: C=54.79%, H=7.98%, N=13.69%

EXAMPLE 22

Synthesis of Z-Arg(Mts)-Leu-Gln-Arg(Mts)-Leu-OH

In 60 ml of dimethylformamide is dissolved 4.9 g (10 millimoles) of Z-Arg(Mts)-OH, and 1.1 ml of N-methylmorpholine is added to the solution. Under cooling to −10° C. and stirring, 0.95 ml of ethyl chloroformate is added to the mixture, and after 5 minutes, 60 ml of a dimethylformamide solution containing 1 ml of N-methylmorpholine and 8.3 g (9.7 millimoles) of a salt of H-Leu-Gln-Arg(Mts)-Leu-OH.CF$_3$COOH obtained by treating 8.0 g (9.4 millimoles) of Boc-Leu-Gln-Arg(Mts)-Leu-OH obtained according to the method of Example 21 with a liquid mixture of 50 ml of methylene chloride and 50 ml of trifluoroacetic acid is dropped to the mixture under cooling. The mixture is stirred at −10° C. for 4.5 hours and allowed to stand still in a low temperature chamber overnight, and added to 600 ml of a 1% aqueous solution of citric acid. The mixture is sufficiently stirred and the formed precipitate is recovered by filtration, washed with water and dried to obtain 10.4 g of intended Z-Arg(Mts)-Leu-Gln-Arg(Mts)-Leu-OH (the yield being 90.6%).

Melting Point:
130°–135° C. (decomposition)

TLC:
Rf value=0.60 (chloroform/methanol=7/3)

Optical Rotation:
$[\alpha]_D^{27} = -17.5°$ (C=1, trifluoroethanol)

Elementary Analysis as $C_{55}H_{82}N_{12}O_{13}S_2.H_2O$:
Calculated: C=54.98%, H=7.05%, N=13.99%
Found: C=55.27%, H=7.01%, N=13.96%

EXAMPLE 23

Synthesis of Z-Arg(Mts)-Leu-Gln-Arg(Mts)-Leu-Leu-Gln-Gly-Leu-Val-NH$_2$

In 100 ml of dimethylformamide are dissolved 4.2 g (3.55 millimoles) of Z-Arg(Mts)-Leu-Gln-Arg(Mts)-Leu-OH obtained in Example 22 and 0.82 g of N-hydroxysuccinimide. The solution is cooled to −10° C. and 0.88 g of dicyclohexylcarbodiimide is added, and the mixture is stirred for 3 hours and further stirred in a low temperature chamber (2° to 3° C.) for 1.5 days. Separately, 2.0 g (3.55 millimoles) of CF$_3$COOH.H-Leu-Gln-Gly-Leu-Val-NH$_2$ [obtained by treating Boc-Leu-Gln-Gly-Leu-Val-NH$_2$ having a melting point of 236° to 238° C. and an optical rotation $[\alpha]_D^{20}$ of $-18.9°$ (C=2, DMF) with CF$_3$COOH] is dissolved in 50 ml of DMF and 0.39 ml of N-methylmorpholine is added, and the solution is cooled to 0° C. and added to the above mixture. The resulting mixture is stirred for 1 day in a low temperature chamber and for 2 days at room temperature. It is concentrated under a reduced pressure and added to 300 ml of a 2% aqueous solution of sodium bicarbonate. The formed precipitate is recovered by filtration to obtain 4.4 g (yield=73%) of intended Z-Arg(Mts)-Leu-Gln-Arg(Mts)-Leu-Leu-Gln-Gly-Leu-Val-NH$_2$.

Melting Point:
144°-152° C. (dicomposition)
TLC:
Rf value=0.41 (chloroform/methanol=4/1)
Optical Rotation:
$[\alpha]_D^{27} = -13.0°$ (C=1, trifluoroethanol)
Elementary Analysis as C$_{79}$H$_{125}$N$_{19}$O$_{18}$S$_2$.3H$_2$O:
Calculated: C=54.31%, H=7.56%, N=15.23%
Found: C=54.42%, H=7.32%, N=15.15%

EXAMPLE 24

Synthesis of H-Arg(Mts)-Leu-OH (i) Synthesis of Z-Arg(Mts)-Leu-OBzl

In 300 ml of tetrahydrofuran is dissolved 49.0 g (100 millimoles) of Z-Arg(Mts)-OH, and 11 ml of N-methylmorpholine is added to the solution and the mixture is stirred at $-5°$ C. for 5 minutes. Then, 9.6 ml of ethyl chloroformate is added to the mixture, and a cooled solution of 39.4 g (100 millimoles) of Tos-OH.H-Leu-OBzl and 11 ml of N-methylmorpholine in dimethylformamide is added to the above mixture. The resulting mixture is stirred at $-5°$ to 0° C. for 4 hours and concentrated under reduced pressure. The residue is dissolved in 700 ml of ethyl acetate, and the solution is washed with 0.1 N aqueous hydrochloric acid, 1 N aqueous NaHCO$_3$ and water and concentrated under a reduced pressure to obtain 52 g of intended Z-Arg(Mts)-Leu-OBzl (the yield being 75%) like oil.

(ii) Synthesis of H-Arg(Mts)-Leu-OH

In a liquid mixture of 600 ml of methanol and 20 ml of water is suspended 29 g of Z-Arg(Mts)-Leu-OBzl obtained according to the process (i), and the suspension is stirred for 7 hours in the presence of 3 g of 10% Pd-C in a current of H$_2$. The reaction mixture is heated to dissolve the precipitate and the catalyst is removed by filtration, and the filtrate is concentrated under reduced pressure. Ether is added to the residue to recover 15.4 g of intended H-Arg(Mts)-Leu-OH.

Melting Point:
156°-158° C. (decomposition)
TLC:
Rf value=0.55 (butanol/acetic acid/water=4/1/5)
Optical Rotation:
$[\alpha]_D^{27} = +12.7°$ (C=1, methanol)
Elementary Analysis as C$_{21}$H$_{35}$N$_5$O$_5$S.H$_2$O:
Calculated: C=51.72%, H=7.65%, N=14.36%
Found: C=51.81%, H=7.35%, N=14.26%

EXAMPLE 25

Synthesis of Z-Ser(Bu$^t$)-Arg(Mts)-Leu-OH

In 40 ml of tetrahydrofuran are dissolved 4.43 g (15 millimoles) of Z-Ser(Bu$^t$)-OH and 2.0 g of N-hydroxysuccinimide, and the solution is cooled to 0° C. and 3.1 g of dicyclohexylcarbodiimide is added to the solution. The mixture is stirred for 3 hours at the above temperature and then stirred in a low temperature chamber overnight. The formed precipitate is removed by filtration and the filtrate is concentrated under reduced pressure. The obtained oily substance is dissolved in 10 ml of dimethylformamide. This solution is mixed with a solution formed by dissolving 5.6 g (12 millimoles) of H-Arg(Mts)-Leu-OH prepared according to the process (ii) of Example 24 in 50 ml of dimethylformamide and adding 1.35 ml of N-methylmorpholine to the solution, and the mixture is stirred for 6 hours at 6° C., overnight in a low temperature chamber and for 5 hours at room temperature. The insoluble substances are removed by filtration and the filtrate is concentrated under reduced pressure. The residue is extracted with 300 ml of ethyl acetate, washed with 2% citric acid and water and dried with magnesium sulfate. The dried filtrate is concentrated under a reduced pressure and ether and petroleum ether are added to the residue to effect solidification. 8.5 g of intended Z-Ser(Bu$^t$)-Arg(Mts)-Leu-OH (the yield being 95%) was obtained.

Melting Point:
96°-105° C. (decomposition)
TLC:
Rf value=0.59 (chloroform/methanol=3/1)
Optical Rotation:
$[\alpha]_D^{27} = -9.4°$ (C=1, methanol)
Elementary Analysis as C$_{36}$H$_{54}$N$_6$O$_9$S:
Calculated: C=57.89%, H=7.29%, N=11.25%
Found: C=58.18%, H=7.59%, N=11.54%

EXAMPLE 26

Synthesis of Z-Arg(Mts)-Asp(OBu$^t$)-Ser(Bu$^t$)-Ala-OH

In 130 ml of dimethylformamide is dissolved 7.3 g (14.9 millimoles) of Z-Arg(Mts)-OH, and 1.64 ml of N-methylmorpholine is added to the solution and the mixture is cooled to $-5°$ C. Then, 1.43 ml of ethyl chloroformate is dropped to the mixture under agitation and the mixture is stirred for 15 minutes and is then mixed with a cooled liquid formed by suspending 6.32 g (15.7 millimoles) of H-Asp(OB$^t$)-Ser(Bu$^t$)-Ala-OH (having a melting point of 122° to 133° C.) in 150 ml of dimethylformamide and adding 1.73 ml of N-methylmorpholine. The resulting mixture is stirred for 3 hours, and the insoluble substances are removed by filtration. The filtrate is concentrated under a reduced pressure and the residue is treated with 5% citric acid solution and ether to obtain 8.8 g of intended Z-Arg(Mts)-Asp(OBu$^t$)-Ser(Bu$^t$)-Ala-OH (the yield being 67%).

Melting Point:
110°-120° C. (decomposition)
TLC:
Rf value=0.34 (chloroform/methanol=4/1)
Optical Rotation:
$[\alpha]_D^{21} = -10.80$ (C=1, trifluoroethanol)
Elementary Analysis as C$_{41}$H$_{61}$N$_7$O$_{12}$S:
Calculated: C=56.21%, H=7.02%, N=11.19%
Found: C=55.93%, H=7.30%, N=10.94%

EXAMPLE 27

Synthesis of Z-Ser(Bu$^t$)-Arg(Mts)-Leu-Arg(Mts)-Asp(OBu$^t$)-Ser(Bu$^t$)-Ala-OH In 30 ml of dimethylformamide are dissolved 5.98 g (8.0 millimoles) of Z-Ser(Bu$^t$)-Arg(Mts)-Leu-OH and 1.01 g of N-hydroxysuccinimide, and the solution is cooled to −5° C. and 1.65 g of dicyclohexylcarbodiimide is added to the solution under agitation. The mixture is stirred at −5° C. for 3 hours and allowed to stand still in a low temperature chamber overnight. Separately, 8.0 g of Z-Arg(Mts)-Asp(OBu')-Ser(Bu')-Ala-OH obtained according to the method of Example 26 is reacted in the presence of 10% Pd-C in 80% trifluoroethanol in a current of $H_2$ for 6 hours, and 5.79 g (7.8 millimoles) of the resulting Z-free derivative of the above compound is suspended in 40 ml of dimethylformamide. Then, 0.86 ml of N-methylmorpholine is added to the suspension and the mixture is stirred and cooled.

The mixture is then added to the above liquid reaction mixture, and the resulting mixture is stirred at 0° C. for 6 hours, allowed to stand in a low temperature chamber overnight and then stirred at 0° C. for 6 hours. The formed precipitate is separated by filtration, and the filtrate is concentrated under reduced pressure and the residue is added to 400 ml of 0.05 M citric acid. The formed precipitate is recovered by filtration, washed with water and dissolved in a mixed liquid of trifluoroethanol, methanol and chloroform. The solution is concentrated under reduced pressure and ethyl acetate is added to the concentrate, and the formed precipitate is recovered by filtration to obtain 29.1 g of intended Z-Ser(Bu')-Arg(Mts)-Leu-Arg(Mts)-Asp(OBu')-Ser(Bu')-Ala-OH (the yield being 62%).

Melting Point:
173°–176° C. (decomposition)
TLC:
Rf value=0.41 (chloroform/methanol=5/1)
Optical Rotation:
$[\alpha]_D^{21} = -8.4°$ (C=1, trifluoroethanol)
Elementary Analysis as $C_{69}H_{107}N_{13}O_{18}S_2 \cdot C_2H_5OC_2H_5$:
Calculated: C=56.75%, H=7.63%, N=11.78%
Found: C=57.02%, H=7.92%, N=12.08%

EXAMPLE 28

Synthesis of Z-Ser(Bu')-Arg(Mts)-Leu-Arg(Mts)-Asp(OBu')-Ser(Bu')-Ala-Arg(Mts)-Leu-Gln-Arg(Mts)-Leu-Leu-Gln-Gly-Leu-Val-NH$_2$ To 23 ml of dimethylformamide is added 173 mg of N-hydroxysuccinimide, and 1.84 g (1.254 millimoles) of Z-Ser(Bu')-Arg(Mts)-Leu-Arg(Mts)-Asp(OBu')-Ser(Bu')-Ala-OH is dissolved therein. Then, 2.0 g (1.254 millimoles) of ACOH.H-Arg(Mts)-Leu-Gln-Arg(Mts)-Leu-Leu-Gln-Gly-Leu-Val-NH$_2$ obtained by reducing 2.64 g of the Z-compound obtained according to the method of Example 23 in the presence of 10% Pd-C in 80% acetic acid is added to the solution, and 1.3 ml of a dimethylformamide (DMF) solution of N-methylmorpholine (1 millimole per ml of DMF) is further added. The mixture is cooled to −10° C. and a dimethylformamide solution containing 284 mg of dicyclohexylcarbodiimide is added to the mixture under agitation. Reaction is conducted for 3 hours, and the mixture is stirred in a low temperature room (4° C.) for 2.5 days and at room temperature for 1 day. The mixture is concentrated under a reduced pressure, and the residue is added to water. The formed precipitate is treated with chloroform/methanol/ether to obtain 2.0 g of intended Z-Ser(Bu')-Arg(Mts)-Leu-Arg(Mts)-Asp(OBu')-Ser(Bu')-Ala-Arg(Mts)-Leu-Gln-Arg(Mts)-Leu-Leu-Gln-Gly-Leu-Val-NH$_2$ (the yield being 53.0%).

Melting Point:
150°–160° C. (decomposition)
TLC:
Rf value=0.51 (chloroform/methanol=5/1)
Optical Rotation:
$[\alpha]_D^{24} = -7.8°$ (C=2, trifluoroethanol)
Elementary Analysis as $C_{140}H_{224}N_{32}O_{33}S_4 \cdot 4H_2O$:
Calculated: C=54.52%, H=7.58%, N=14.54%
Found: C=54.54%, H=7.42%, N=14.44%

The above mentioned Z-free derivative will be illustrated in respect to the preparation and its physical properties.

ACOH.H-Arg(Mts)-Leu-Gln-Arg(Mts)-Leu-Leu-Gln-Gly-Leu-Val-NH$_2$ 2.64 g (1.56 millimoles) of Z-Arg(Mts)-Leu-Gln-Arg(Mts)-Leu-Leu-Gln-Gly-Leu-Val-NH$_2$ was dissolved in 150 ml of an aqueous 80% acetic acid solution. Then hydrogen gas was introduced into the resulting solution over a period of 8 hours, while agitated, in the presence of 300 mg of 10% Pd-C. The Pd-C was filtrated out, and the filtrate was concentrated under a reduced pressure and the residue was dissolved in trifluoroethanol. The solution was treated by filtration and concentrated. Ether was added to the residue and the produced precipitate was reparated by filtration. In this was 2.1 g (yield 84%) of ACOH.H-Arg(Mts)-Leu-Gln-Arg(Mts)-Leu-Leu-Gln-Gly-Leu-Val-NH$_2$.

Physical properties thereof are:
Melting Point:
150°–153° C. (decomposition)
TLC:
Rf value=0.32 (chloroform/methanol=4/1)
Optical Rotation:
$[\alpha]_D^{28} = -33.6°$ (C=1.1 acetic acid)
Elementary Analysis as $C_{71}H_{119}N_{19}O_{16}S_2 \cdot CH_3COOH \cdot 5/3 CF_3CH_2OH$
Calculated: C=51.34%, H=7.23%, N=14.30%
Found: C=51.04%, H=7.28%, N=15.20%

EXAMPLE 29

Synthesis of Protected Secretin, Boc-His(Boc)-Ser(Bu')-Asp(OBu')-Gly-Thr(Bu')-Phe-Thr(Bu')-Ser(Bu')-Glu(OBu')-Leu-Ser(Bu')-Arg(Mts)-Leu-Arg(Mts)-Asp(OBu')-Ser(Bu')-Ala-Arg(Mts)-Leu-Gln-Arg(Mts)-Leu-Leu-Gln-Gly-Leu-Val-NH$_2$ In a mixed liquid of 20 ml of dimethylformamide and 20 ml of N-methylpyrrolidone are dissolved 577 mg (0.354 millimoles) of Boc-His(Boc)-Ser(Bu')-Asp(OBu')-Gly-Thr(Bu')-Phe-Thr(Bu')-Ser(Bu')-Glu(OBu')-Leu-OH obtained according to the method of Example 15, 850 mg (0.295 millimoles) of HCl.H-Ser(Bu')-Arg(Mts)-Leu-Arg(Mts)-Asp(OBu')-Ser(Bu')-Ala-Arg(Mts)-Leu-Gln-Arg(Mts)-Leu-Leu-Gln-Gly-Leu-Val-NH$_2$ (Z is removed by H$_2$ from the Z-compound obtained according to the method of Example 28 in the presence of 10% Pd-C in 80% acetic acid and the resulting Z-free compound is converted to a hydrochloride) and 57 mg of N-hydroxysuccinimide. The solution is cooled and 0.3 ml of a dimethylformamide solution containing 1 millimole of N-methylmorpholine per ml of DMF is added to the solution. Then, 88 mg of dicyclohexylcarbodiimide is added to the solution, and the solution is stirred in an ice chamber for 1 day and reaction is then carried out at room temperature for 3 days. The reaction mixture is added to a liquid mixture of water and ether, and the formed precipitate is recovered by filtration to obtain 1.4 g of a crude product of the intended protected secretin, Boc-His(Boc)-Ser(Bu')

-Asp(OBu')-Gly-Thr(Bu')-Phe-Thr(Bu')-Ser(Bu')-Glu(OBu')-Leu-Ser(Bu')-Arg(Mts)-Leu-Arg(Mts)-Asp(OBu')-Ser(Bu')-Ala-Arg(Mts)-Leu-Gln-Arg(Mts)-Leu-Leu-Gln-Gly-Leu-Val-NH₂. The crude product is purified by silica gel chromatography Wako Gel C200, 3.5 cm in diameter and 20 cm in length, elution with chloroform/methanol) to obtain 698 mg of the intended product (the yield being 51%).

Melting Point:
248°–255° C. (decomposition)

TLC:
Single spot, Rf value=0.48 (chloroform/methanol=6/1)

Optical Rotation:
$[\alpha]_D^{21} = 6.3°$ (C=1, trifluoroethanol/chloroform=⅓)

Elementary Analysis as $C_{212}H_{348}N_{44}O_{53}S_4 \cdot 5H_2O$:
Calculated: C=55.60%, H=7.88%, N=13.46%
Found: C=55.50%, H=8.06%, N=13.18%

EXAMPLE 30

Synthesis of Crude Secretin:

(i) In a closed hydrogen fluoride (HF) reaction vessel, 1.0 g of the protected secretin obtained in Example 29 is dissolved in 20 ml of HF in the presence of 2 ml of anisole at −5° C., and the mixture is stirred for 1 hour while distilling HF from the reaction system. The residue is washed with ether, dissolved in cold water and converted to an acetate by treatment with Amberlite IRA-93 (acetic acid type). Then, the acetate is freeze-dried to obtain 0.68 g of white powdery crude secretin (yield 90%).

(ii) 630 mg of the protected secretin obtained in Example 29 is dissolved in 10 ml of a mixture of trifluoromethane sulfonic acid and trifluoroacetic acid (1/1) in the presence of 0.4 ml of anisole at −10° C., and the mixture is stirred for 1 hour. Ether is added to the mixture and the clear upper portion thereof is decanted. The residue is dissolved in cold water and converted to an acetate thereof by treatment with Amberlite IRA-93 (the acetic acid type). Then, the acetate is freeze-dried to obtain 410 mg of white powdery crude secretin (yield 86%).

EXAMPLE 31

Purification of crude secretin

In 50 ml of water is dissolved 600 mg of the crude secretin obtained in Example 30, and the solution is charged in a column (3.2 cm in diameter and 32 cm in length) of carboxymethyl cellulose (Whatman CM-52) and elution is carried out with 0.05 M ammonium acetate and 0.13 M ammonium acetate. Each fraction consists of 210 drops. Good secretin eluate is contained in 116th to 185th drops in each fraction. The secretin-containing drops are combined and freeze-dried to obtain 486 mg of purified secretin (the yield being 81%). The biological activity of this purified secretin is about 4500 cu/mg, and from the amino acid analysis, it is found that the peptide content is about 86%. By the disc electrophoreiss, thin layer chromatography and high speed liquid chromatography, it is confirmed that the obtained purified product is a single substance.

The purified secretin obtained according to the process of this Example has an activity of about 5200 cu/mg as the dry free base, and it is found that the product has a very high activity.

TLC:
Rf value=0.54 (butanol/acetic acid/pyridine/water=15/5/5/8)

Optical Rotation:
$[\alpha]_D^{16} = -56.8°$ (C=0.4, 0.01 N HCl)
$[\alpha]_D^{25} = -48.9°$ (C=1.0, 1 N-acetic acid)

Amino Acid Analysis Values: His 0.99 (1), Arg 4.15 (4), Asp 1.97 (2), Thr 1.92 (2), Ser 4.10 (4), Glu 2.89 (3), Gly 1.97 (2), Ala 1.02 (1), Val 0.98 (1), Leu 6.12 (6), Phe 1.00 (1), peptide content=86%

The embodiments of the invention in which an exelusine property or privilege is claimed are defined as follows:

1. A heptacosapeptide having the following structural formula:

Boc-His(Boc)-Ser(Bu')-Asp(OBu')-Gly-Thr(Bu')-Phe-Thr(Bu')-Ser(Bu')-Glu-(OBu')-Leu-Ser(Bu')-Arg(X)-Leu-Arg(X)-Asp(OBu')-Ser(Bu')-Ala-Arg(X)-Leu-Gln-Arg(X)-Leu-Leu-Gln-Gly-Leu-Val-NH₂, in which X is a group having the formula:

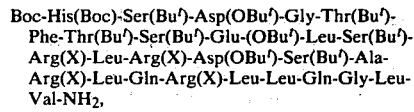

wherein R is alkyl or alkoxy and m is an integer of 1 to 3, provided that the R's are the same or different when m is 2 or 3.

2. A heptacosapeptide as claimed in claim 1, in which X is tosyl.

3. A heptacosapeptide as claimed in claim 1, in which X is mesitylene-2-sulfonyl.

4. A process for the preparation of a heptacosapeptide having the following structural formula:

Boc-His(Boc)-Ser(Bu')-Asp(OBu')-Gly-Thr(Bu')-Phe-Thr(Bu')-Ser(Bu')-Glu(OBu')-Leu-Ser(Bu')-Arg(X)-Leu-Arg(X)-Asp(OBu')-Ser(Bu')-Ala-Arg(X)-Leu-Gln-Arg(X)-Leu-Leu-Gln-Gly-Leu-Val-NH₂, in which X is a group having the formula

wherein R is alkyl or alkoxy and m is an integer of 1 to 3, provided that the R's are the same or different when m is 2 or 3, which comprises condensing a decapeptide having the following structural formula:

Boc-His(Boc)-Ser(Bu')-Asp(OBu')-Asp(OBu')-Gly-Thr(Bu')-Phe-Thr(Bu')-Ser(Bu')-Glu(OBu')-Leu-OH with a heptadecapeptide having the following structural formula:

H-Ser(Bu')-Arg(Tos)-Leu-Arg(X)-Asp(OBu')-Ser(-Bu')-Ala-Arg(X)-Leu-Gln-Arg(X)-Leu-Leu-Gln-Gly-Leu-Val-NH₂.

5. A process for the preparation of a heptacosapeptide having the following structural formula:

Boc-His(Boc)-Ser(Bu')-Asp(OBu')-Gly-Thr(Bu')-Phe-Thr(Bu')-Ser(Bu')-Glu(OBu')-Leu-Ser(Bu')-Arg(X)-Leu-Arg(X)-Asp(OBu')-Ser(Bu')-Ala-

Arg(X)-Leu-Gln-Arg(X)-Leu-Leu-Gln-Gly-Leu-
Val-NH₂, in which X is a group having the formula

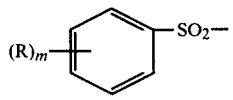

wherein R is alkyl or alkoxy and m is an integer of 1 to 3, provided that the R's are the same or different when m is 2 or 3, which comprises condensing a hexacosapeptide having the following structural formula:

H-Ser(Buᵗ)-Asp(OBuᵗ)-Gly-Thr(Buᵗ)-Phe-Thr(Buᵗ)-
Ser(Buᵗ)-Glu(OBuᵗ)-Leu-Ser(Buᵗ)-Arg(X)-Leu-
Arg(X)-Asp(OBuᵗ)-Ser(Buᵗ)-Ala-Arg(X)-Leu-
Gln-Arg(X)-Leu-Leu-Gln-Gly-Leu-Val-NH₂, with Boc-His(Boc).ONP.

6. A process for the preparation of a heptacosapeptide having the following structural formula:

Boc-His(Boc)-Ser(Buᵗ)-Asp(OBuᵗ)-Gly-Thr(Buᵗ)-
Phe-Thr(Buᵗ)-Ser(Buᵗ)-Glu(OBuᵗ)-Leu-Ser(Buᵗ)-
Arg(X)-Leu-Arg(X)-Asp(OBuᵗ)-Ser(Buᵗ)-Ala-
Arg(X)-Leu-Gln-Arg(X)-Leu-Leu-Gln-Gly-Leu-
Val-NH₂, in which X is a group having the formula

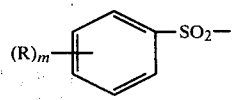

wherein R is alkyl or alkoxy and m is an integer of 1 to 3, provided that the R's are the same or different when m is 2 or 3, which comprises condensing a heptapeptide having the following structural formula:

Z-Ser(Buᵗ)-Arg(X)-Leu-Arg(X)-Asp(OBuᵗ)-Ser(-
Buᵗ)-Ala-OH with a decapeptide having the following structural formula:

H-Arg(X)-Leu-Gln-Arg(X)-Leu-Leu-Gln-Gly-Leu-
Val-NH₂ to form a heptadecapeptide having the following structural formula:

Z-Ser(Buᵗ)-Arg(X)-Leu-Arg(X)-Asp(OBuᵗ)-Ser(-
Buᵗ)-Ala-Arg(X)-Leu-Gln-Arg(X)-Leu-Leu-Gln-
Gly-Leu-Val-NH₂, subjecting said heptadecapeptide to catalytic reduction to form a Z-free product having the following structural formula:

H-Ser(Buᵗ)-Arg(X)-Leu-Arg(X)-Asp(OBuᵗ)-Ser(-
Buᵗ)-Ala-Arg(X)-Leu-Gln-Arg(X)-Leu-Leu-Gln-
Gly-Leu-Val-NH₂, and condensing said Z-free
product with a decapeptide having the following
structural formula:

Boc-His-Boc)-Ser(Buᵗ)-Asp(OBuᵗ)-Gly-Thr(Buᵗ)-
Phe-Thr(Buᵗ)-Ser(Buᵗ)-Glu(OBuᵗ)-Leu-OH.

7. A decapeptide having the formula:

Boc-His(Boc)-Ser(Buᵗ)-Asp(OBuᵗ)-Gly-Thr(Buᵗ)-
Phe-Thr(Buᵗ)-Ser(Buᵗ)-Glu(OBuᵗ)-Leu-OH

8. A heptadecapeptide having the formula:

H-Ser(Buᵗ)-Arg(X)-Leu-Arg(X)-Asp(OBuᵗ)-Ser(-
Buᵗ)-Ala-Arg(X)-Leu-Gln-Arg(X)-Leu-Leu-Gln-
Gly-Leu-Val-NH₂, in which X is a group having the formula

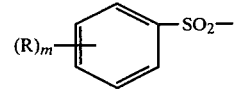

wherein R is alkyl or alkoxy and m is an integer of 1 to 3, provided that the R's are the same or different when m is 2 or 3, and a salt thereof.

9. A decapeptide having the formula:

H-Arg(X)-Leu-Gln-Arg(X)-Leu-Leu-Gln-Gly-Leu-
val-NH₂, in which X is a group having the formula

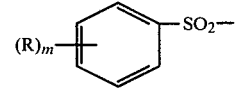

wherein R is alkyl or alkoxy and m is an integer of 1 to 3, provided that the R's are the same or different when m is 2 or 3, and a salt thereof.

10. A heptapeptide having the formula:

Z-Ser(Buᵗ)-Arg(X)-Leu-Arg(X)-Asp(OBuᵗ)-Ser(-
Buᵗ)-Ala-OH, in which X is a group having the formula

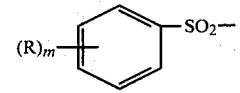

wherein R is alkyl or alkoxy and m is an integer of 1 to 3, provided that the R's are the same or different when m is 2 or 3.

11. A process for manufacturing a secretin, which comprises treating a heptacosapeptide having the formula:

Boc-His(Boc)-Ser(Buᵗ)-Asp(OBuᵗ)-Gly-Thr(Buᵗ)-
Phe-Thr(Buᵗ)-Ser(Buᵗ)-Glu(OBuᵗ)-Leu-Ser(Buᵗ)-
Arg(X)-Leu-Arg(X)-Asp(OBuᵗ)-Ser(Buᵗ)-Ala-
Arg(X)-Leu-Gln-Arg(X)-Leu-Leu-Gln-Gly-Leu-
Val-NH₂, in which X is a group having the formula:

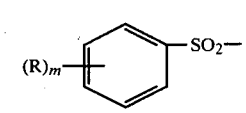

wherein R is an alkyl or alkoxy and m is an integer of 1 to 3, provided that the R's are the same or different when m is 2 or 3, with a strong acid in order to remove the protective groups attached to said heptacosapeptide.

* * * * *

UNITED STATES PATENT AND TRADEMARK OFFICE
CERTIFICATE OF CORRECTION

PATENT NO. : 4 407 745
DATED : October 4, 1983
INVENTOR(S) : Mikio UCHIYAMA et al It is certified that error appears in the above-identified patent and that said Letters Patent is hereby corrected as shown below:

Column 24, Line 15; change to read as follows:

---Phe-Thr($Bu^t$)-Ser($Bu^t$)-Glu($OBu^t$)-Leu-Ser($Bu^t$)- ---.

Column 24, Line 55; change to read as follows:

---Boc-His(Boc)-Ser($Bu^t$)-Asp($OBu^t$)-Gly- ---.

Column 26, Line 20; change "val-$NH_2$," to ---Val-$NH_2$,---.

Signed and Sealed this

Third Day of January 1984

[SEAL]

Attest:

GERALD J. MOSSINGHOFF

Attesting Officer   Commissioner of Patents and Trademarks